US00PP08984P

United States Patent [19]

Heims

[11] Patent Number: Plant 8,984

[45] Date of Patent: Nov. 22, 1994

[54] HEUCHERA 'PEWTER VEIL'

[75] Inventor: Dan M. Heims, Portland, Oreg.

[73] Assignee: Terra-Nova Nurseries, Inc., Portland, Oreg.

[21] Appl. No.: 175,934

[22] Filed: Dec. 30, 1993

[51] Int. Cl.[5] ..... A01H 5/00
[52] U.S. Cl. ..... Plt./68.1
[58] Field of Search ..... Plt. 68.1

*Primary Examiner*—James R. Feyrer
*Attorney, Agent, or Firm*—Klarquist Sparkman Campbell Leigh & Whinston

[57] ABSTRACT

A new and distinct variety of Heuchera having a unique metallic finish and coloration on evergreen foliage in U.S.D.A. zone 7 and above, and leaves that turn to a pewter sheen in summer.

1 Drawing Sheet

The present invention relates to a new and distinct hybrid of Heuchera which originated as a cross-pollination of Heuchera "Montrose Ruby" and *Heuchera americana* "Dale's Strain" in the Saxifragaceae family.

The new Heuchera is a result of a controlled cross of the aforementioned plants at Terra-Nova Nursery in Portland, Ore. This hybrid was selected from a large selection of seedlings. Mother plants were retained to observe habit and to compare with their progeny. The new variety has been reproduced only by asexual propagation (division and tissue culture). Each of the progeny exhibits identical characteristics to the original plant and is unlike any Heuchera offered by any American nursery or book as evidenced by the following characteristics:

(1) Spring, fall and winter pink metallic bronze coloration on the foliage.

(2) Summer metallic foliage of a pewter hue. (Jun.-Aug.).

Asexual propagation by division and tissue cultures done in Mt. Vernon, Wash. shows that the foregoing characteristics and distinctions come true to form and are established and transmitted through succeeding propagations.

BRIEF DESCRIPTION OF THE PHOTOGRAPHS

DETAILED PLANT DESCRIPTION

Figure 1:
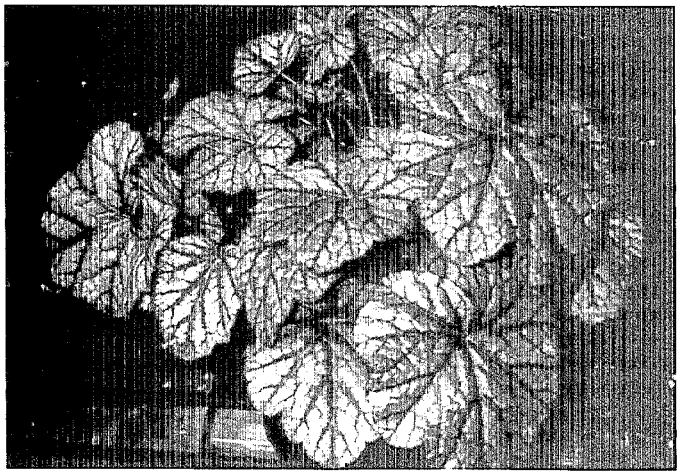
FIG. 1 is a picture in the greenhouse showing the metallic bronze-pink foliage.
Figure 2:
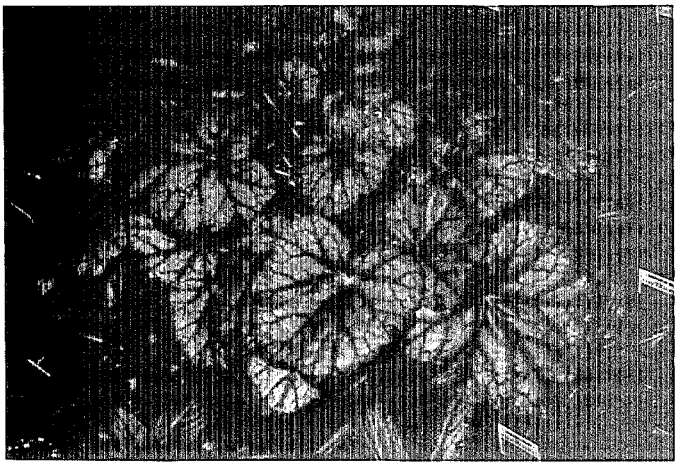
FIG. 2 is a summer picture showing the pewter coloration.

The following is a detailed description of the new Heuchera hybrid based on observations of specimens in Portland, Ore. The color descriptions are all based on The Royal Horticultural Society Color Chart.

Foliage:

*Type.*—Evergreen, herbaceous in a hard winter.
*Shape.*—Rounded cordate, 7 lobed.
*Length.*—10 to 14 cm (4 to 5½ in).
*Width.*—11 to 15 cm (4¼ to 6 in).
*Petiole length.*—14 to 20 cm (5½ to 8 in).
*Margins.*—Crenate, ciliate.
*Apex.*—Broadly obtuse, lobed.
*Base.*—Cordate.

*Texture.*—Rugose, glabrous, pruinose.
*Leaf arrangement.*—Basal leaves tufted.
*Venation.*—Reticulate.

Flower:

*Petal count.*—5 petals.
*Petal shape.*—Spatulate, recurved. Entire margin.
*Flower type.*—Complete, calyx tube urn-shaped, stamens exserted.
*Flower size.* 1 to 1.25 cm (0.4 to 0.5 in).
*Blooming habit.*—Paniculate to 70 cm.
*Bloom period.*—May to August.

Color Characteristics

Foliage:

*Mature leaves upper surface.*—Fall through spring: Red-Purple Group 65C as metallic.
*Summer color.*—Greyed-Green Group 198A as metallic.
*Veins (upper surface).*—Black Group 202A, underlaid by Green Group 131A.
*Lower surface.*—Red-Purple Group 71A.

Flowers: Yellow-Green Group 145D on paniculate stems of Red-Purple Group 71A.

DESCRIPTION OF PARENT PLANTS

This Heuchera hybrid has characteristics which make it unique from its parents: *Heuchera americana* "Dale's Strain" and Heuchea "Montrose Ruby". *Heuchera americana* "Dale's Strain" is described in the North Creek Nurseries catalog as having marbled silver and green leaves. Heuchera "Montrose Ruby" is described in the catalogue of Montrose Nursery (closing in 1994) as a cross between *Heuchera micrantha* "Palace Purple" and *Heuchera americana* "Dale's Strain". The ensuing plants have Bronze-metallic leaves without the pronounced veining and pink hue of Heuchera "Pewter Veil". No other Heuchera in commerce resemble Heuchera "Pewter Veil".

I claim:

1. A new and distinct hybrid of Heuchera substantially as shown and described, characterized by unique metallic finish and coloration on evergreen foliage in U.S.D.A. zone 7 and above, and leaves that turn to a pewter sheen in summer.

* * * * *